United States Patent
Ekelund et al.

(10) Patent No.: US 10,010,424 B2
(45) Date of Patent: Jul. 3, 2018

(54) IMPLANT

(71) Applicant: DEPUY IRELAND UNLIMITED COMPANY, County Cork (IE)

(72) Inventors: Anders Ekelund, Bromma (SE); Sylvain Gauthier, Lyons (FR)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 2 days.

(21) Appl. No.: 15/453,507

(22) Filed: Mar. 8, 2017

(65) Prior Publication Data

US 2017/0172750 A1 Jun. 22, 2017

Related U.S. Application Data

(62) Division of application No. 14/008,597, filed as application No. PCT/EP2012/052463 on Feb. 14, 2012, now Pat. No. 9,622,870.

(51) Int. Cl.
*A61F 2/30* (2006.01)
*A61F 2/40* (2006.01)
(Continued)

(52) U.S. Cl.
CPC .......... *A61F 2/4014* (2013.01); *A61B 17/746* (2013.01); *A61F 2/30728* (2013.01);
(Continued)

(58) Field of Classification Search
CPC ...... A61F 2/40; A61F 2/30; A61F 2/34; A61F 2002/3429; A61F 2002/3631; A61F 2/4014; A61F 2002/30538; A61F 2/4059; A61F 2002/30604; A61F 2002/4037; A61F 2002/4044; A61F 2002/30578; A61F 2/4612
See application file for complete search history.

(56) References Cited

U.S. PATENT DOCUMENTS

| | | |
|---|---|---|
| 2,381,050 A | 8/1945 | Hardinge |
| 2,397,545 A | 4/1946 | Hardinge |
(Continued)

FOREIGN PATENT DOCUMENTS

| | | |
|---|---|---|
| DE | 10123517 C1 | 11/2002 |
| DE | 102006047663 A1 | 4/2008 |
(Continued)

*Primary Examiner* — Ann Schillinger

(57) ABSTRACT

An implant, prosthesis and method of use are described. The implant comprises an articulation component having a bearing surface and a reverse surface arranged to couple to a proximal neck portion of an arthroplasty implant coupled to a bone. A collar is arranged to couple to the reverse surface of the articulation component. The collar defines a neck hole arranged to pass around the coupling between the articulation component and the proximal neck portion of the arthroplasty implant. The collar and the articulation component comprise complementary coupling features to secure the collar to the articulation component. The collar further comprises a plurality of attachment portions to couple the collar to bone fragments or soft tissues. The prosthesis comprises the implant and an arthroplasty implant having a distal portion arranged to be coupled to an end of a long bone and a proximal neck portion.

6 Claims, 5 Drawing Sheets

(51) Int. Cl.
*A61F 2/46* (2006.01)
*A61B 17/74* (2006.01)

(52) U.S. Cl.
CPC .......... *A61F 2/4059* (2013.01); *A61F 2/4637* (2013.01); *A61F 2/4684* (2013.01); *A61F 2002/3055* (2013.01); *A61F 2002/30247* (2013.01); *A61F 2002/30332* (2013.01); *A61F 2002/30367* (2013.01); *A61F 2002/30433* (2013.01); *A61F 2002/30461* (2013.01); *A61F 2002/30729* (2013.01)

(56) References Cited

U.S. PATENT DOCUMENTS

| | | |
|---|---|---|
| 2,612,159 A | 9/1952 | Collison |
| 3,374,786 A | 3/1968 | Callender, Jr. |
| 3,554,193 A | 1/1971 | Konstantinou |
| 4,005,495 A | 2/1977 | Locke |
| 4,045,825 A * | 9/1977 | Stroot ................ A61F 2/40 623/19.14 |
| 4,101,985 A | 7/1978 | Baumann |
| 4,129,903 A | 12/1978 | Huggler |
| 4,438,762 A | 3/1984 | Kyle |
| 4,612,920 A | 9/1986 | Lower |
| 4,657,001 A | 4/1987 | Fixel |
| 4,686,971 A | 8/1987 | Harris et al. |
| 4,776,329 A | 10/1988 | Treharne |
| 4,791,918 A | 12/1988 | Von Hasselbach |
| 4,795,473 A | 1/1989 | Grimes |
| 4,904,264 A | 2/1990 | Scheunemann |
| 4,976,740 A | 12/1990 | Kleiner |
| 4,998,937 A | 3/1991 | Grimes |
| 5,087,260 A | 2/1992 | Fixel |
| 5,197,989 A | 3/1993 | Hinckfuss |
| 5,376,125 A | 12/1994 | Winkler |
| 5,376,126 A | 12/1994 | Lin |
| 5,569,263 A | 10/1996 | Hein |
| 5,645,607 A | 7/1997 | Hickey |
| 5,658,339 A | 8/1997 | Tronzo |
| 5,725,597 A | 3/1998 | Hwang |
| 5,733,292 A | 3/1998 | Gustilo |
| 5,766,263 A | 6/1998 | Grundei |
| 5,800,553 A | 9/1998 | Albrektsson |
| 5,800,554 A | 9/1998 | Scholz |
| 5,800,557 A | 9/1998 | Elhami |
| 6,139,552 A | 10/2000 | Horiuchi |
| 6,228,120 B1 * | 5/2001 | Leonard ................ A61F 2/4014 623/18.11 |
| 6,375,684 B1 | 4/2002 | Kriek |
| 7,097,663 B1 | 8/2006 | Nicol |
| 7,135,023 B2 | 11/2006 | Watkins |
| 7,425,214 B1 | 9/2008 | McCarthy |
| 8,092,466 B2 | 1/2012 | Splieth |
| RE43,482 E | 6/2012 | Mikol |
| 8,968,409 B2 | 3/2015 | Chavarria |
| 2002/0107520 A1 | 8/2002 | Hoffman |
| 2002/0193797 A1 | 12/2002 | Johnson |
| 2003/0028253 A1 | 2/2003 | Stone |
| 2003/0069582 A1 | 4/2003 | Culbert |
| 2003/0187512 A1 | 10/2003 | Frederick |
| 2005/0197712 A1 | 9/2005 | Bigsby |
| 2006/0009852 A1 | 1/2006 | Winslow |
| 2006/0116679 A1 | 6/2006 | Lutz |
| 2006/0200249 A1 | 9/2006 | Beguin |
| 2006/0217720 A1 | 9/2006 | Chieng |
| 2008/0177395 A1 | 7/2008 | Stinnette |
| 2010/0023131 A1 | 1/2010 | Crofford |
| 2010/0331990 A1 | 12/2010 | Mroczkowski |
| 2013/0035761 A1 | 2/2013 | Sharkey |
| 2013/0197652 A1 | 8/2013 | Ekelund |
| 2013/0338780 A1 | 12/2013 | Berchoux |
| 2014/0094855 A1 | 4/2014 | Chavarria |
| 2014/0114425 A1 | 4/2014 | Ekelund |
| 2014/0121709 A1 | 5/2014 | Gonzalez-Hernandez |
| 2014/0121713 A1 | 5/2014 | Meulink |

FOREIGN PATENT DOCUMENTS

| | | |
|---|---|---|
| DE | 102008053566 A1 | 6/2009 |
| EP | 1952788 A1 | 8/2008 |
| FR | 2946863 A1 | 12/2010 |
| GB | 2007980 A | 5/1979 |
| JP | 2004089712 A | 3/2004 |
| WO | WO 1985005027 A1 | 11/1985 |
| WO | WO 1997039693 A1 | 10/1997 |
| WO | WO 2000009038 A2 | 2/2000 |
| WO | WO 2006126238 A2 | 11/2006 |
| WO | WO 2007024980 A2 | 3/2007 |
| WO | WO 2007082925 A2 | 7/2007 |
| WO | WO 2012104285 A1 | 8/2012 |
| WO | WO 2012130517 A1 | 10/2012 |

* cited by examiner

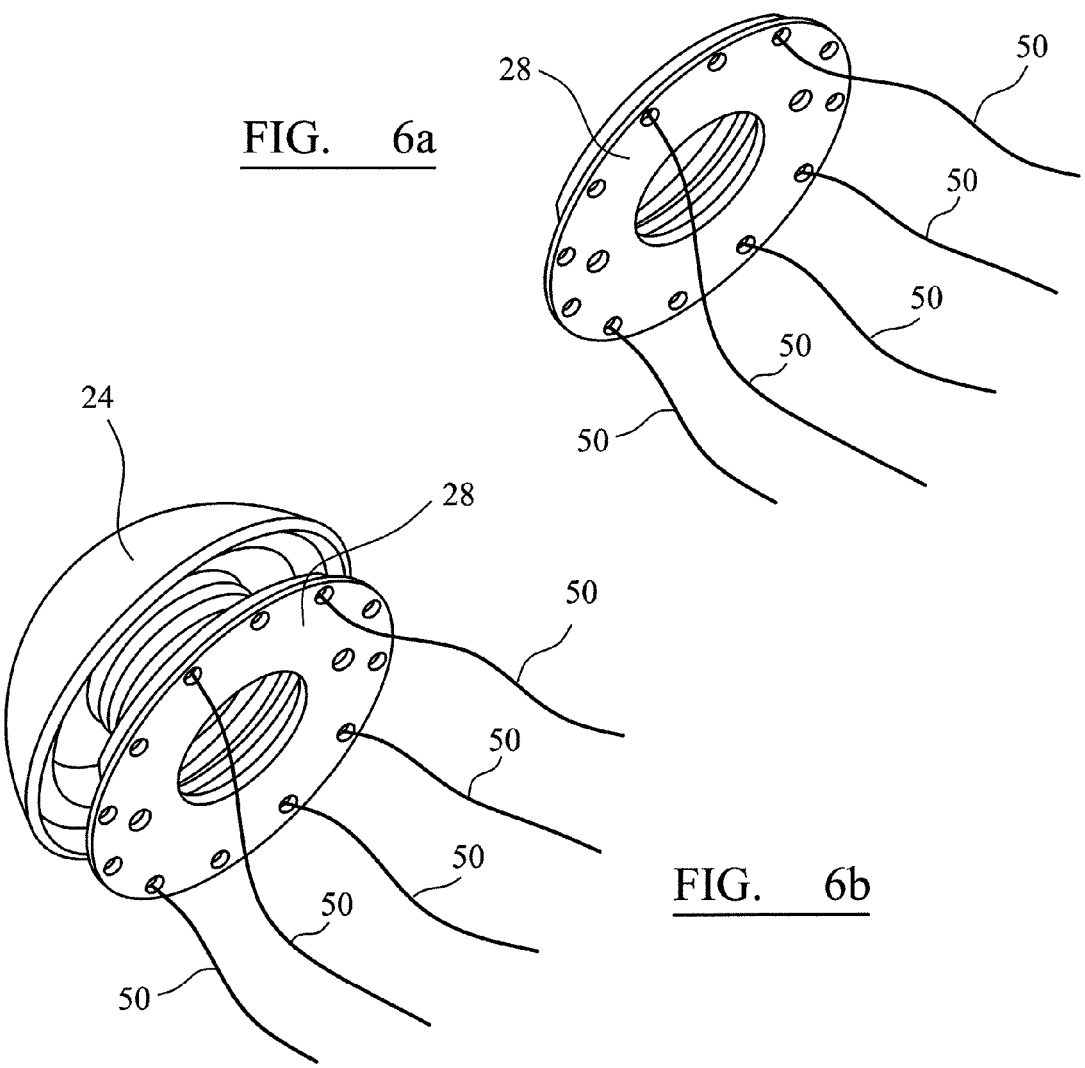
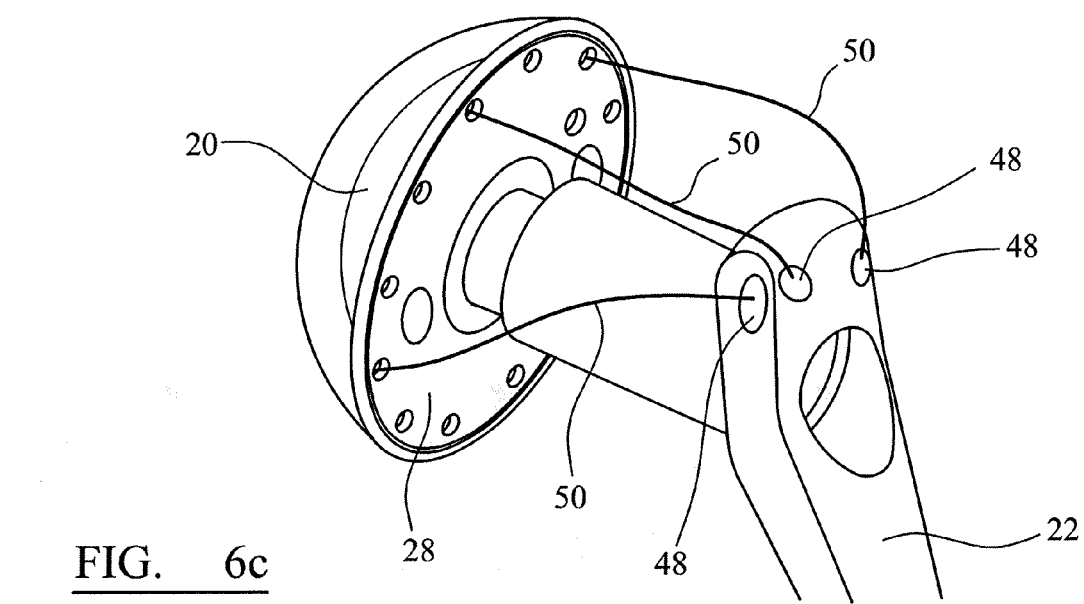

IMPLANT

CROSS REFERENCE TO RELATED APPLICATION

This application is a divisional of U.S. patent application Ser. No. 14/008,597, filed Sep. 30, 2013, which is a National Stage 35 U.S.C. 371 of International Patent Application PCT/EP2012/052463 filed Feb. 14, 2012, which claims priority to United Kingdom Patent Application No. GB1105243.8, filed Mar. 29, 2011 (now abandoned) all of which are incorporated by reference in their entireties.

The present invention relates generally to orthopaedic surgery and in particular to shoulder prostheses. More particularly, the present invention relates to an implant forming part of a humeral prosthesis. Specifically, the implant comprises an articulation component to articulate against a glenoid implant or a natural glenoid cavity. The present invention also relates to an assembled prosthesis and a shoulder arthroplasty procedure using the humeral prosthesis.

A natural shoulder joint may undergo degenerative changes for a variety of reasons, for instance arthritis. Alternatively, a shoulder joint may be fractured or otherwise damaged by an external force. When a shoulder joint is sufficiently degenerated or damaged it may be necessary to replace a natural shoulder joint with a prosthetic shoulder joint. Conventional shoulder prostheses comprise a humeral implant, optionally with a glenoid implant.

Typically, the humeral implant comprises a stem for insertion into a bore extending into the intramedullary canal generally along the longitudinal axis of the bone and an articulation component such as a convex bearing head. Typically, the articulation component is coupled to a neck portion of the stem which extends from the intramedullary canal at an inclined angle relative to the longitudinal axis of a distal portion of the stem in order to recreate the arrangement of the natural joint.

When the upper extremity of the humerus is fractured, the humerus generally breaks into several pieces, typically three or four. In particular, for a four part fracture as illustrated in FIG. 1, the humeral head 2 splits off at the level of the anatomical neck indicated by line 4, the greater tuberosity 6 and lesser tuberosity 8 are separated from the humeral shaft 10 below the tuberosities and the tuberosities 6, 8 are separated from one another along the bicipetal groove 12. In a three part fracture the greater or less tuberosity 6, 8 remains attached to the humeral head 2. For both three part and four part fractures, as there is no longer a blood supply to the humeral head 2 necrosis may begin.

For repair of a four part fracture or a three part fracture, the humeral head is replaced, and the greater and lesser tuberosities are reattached to the humeral shaft. Known shoulder prostheses for repair of a four part fracture provide tabs or fins attached to the stem which incorporate holes to receive sutures to couple the tuberosities and soft tissue such as cuff muscles to the prosthesis. Correct positioning of the suture holes is essential to accommodate the differing attachment points of soft tissues to the humerus in a natural joint. Typically three and four part humeral fractures are repaired through a hemi-arthroplasty procedure as there may be no damage to the glenoid cavity and so no need for its replacement.

Certain known prostheses suffer from inflexibility in the position of attachment points for coupling bone fragments and soft tissues to the implant, which may result in loss of mobility for the repaired joint.

UK patent application 1007656.0 filed on 7 May 2010 in the name of DePuy (Ireland) (and incorporated herein for all purposes) discloses a rotatable collar arranged to couple to a neck portion of a humeral implant, such as a humeral stem which extends into the intramedullary canal. The collar is arranged to be located between an articulation component and the natural bone surrounding the humeral implant. The collar comprises a plate defining a plurality of suture holes or pre-attached sutures around its periphery which allow the detached bone fragments, including the greater and lesser tuberosities to be coupled to the implant. A suture cage may be formed extending from the collar around the detached bone fragments and back to an opposite portion of the plate to hold the bone fragments in position. The collar causes the articulation component to be spaced apart from the bone, and may therefore interfere with the correct positioning of the articulation component.

It is an object of embodiments of the present invention to obviate or mitigate one or more of the problems of the prior art, whether identified herein or elsewhere.

According to a first aspect of the present invention there is provided an implant comprising: an articulation component comprising a bearing surface and a reverse surface arranged to couple to a proximal neck portion of an arthroplasty implant coupled to a bone; and a collar arranged to couple to the reverse surface of the articulation component, the collar defining a neck hole arranged to pass around the coupling between the articulation component and the proximal neck portion of the arthroplasty implant, the collar and the articulation component comprising complementary coupling features to secure the collar to the articulation component; wherein the collar further comprises a plurality of attachment portions to couple the collar to bone fragments or soft tissues.

An advantage of the first aspect of the present invention is that the collar provides a plurality of attachment points for coupling detached bone fragments and soft tissue to the articulation component. As the articulation component and the collar are separate the collar can be positioned in the joint space and bone fragments coupled to the collar without the articulation component in place, which therefore provides the surgeon with more space to operate. The articulation component and the collar can then be coupled together before securing the articulation component to the arthroplasty implant. The collar passing around the coupling between the articulation component and the proximal neck portion such that there is no direct contact between the collar and the proximal neck portion.

In preferred embodiments the collar is received in a recess in a reverse surface of the articulation component such that there is no extra component between the articulation component and the bone and so no gap between the articulation component and the bone due to the collar. The result is that the implant appears as a conventional bearing head implant. When used in combination with an arthroplasty implant supporting additional attachment points, sutures may be provided extending from the collar to the arthroplasty implant to form a cage surrounding the bone fragments. This secures the bone fragments in position and also adds rigidity to the connection between the articulation component and the distal implant component. The present invention is particularly suitable for forming part of a humeral prosthesis to repair three or four part humeral fractures, and in particular for securing bone fragments including the greater and lesser tuberosities.

The reverse surface of the articulation component may comprise a recess and the collar may be arranged to be received in the recess.

The reverse surface of the articulation component may comprise a socket protruding from the base of the recess and arranged to receive the end of the proximal neck portion of an arthroplasty implant, the recess extending annularly between the socket and a rim defining the boundary between the bearing surface and the reverse surface of the articulation component, wherein the neck hole of the collar is arranged to pass over the socket.

The complementary coupling features may comprise the recess and the collar having corresponding screw threads. Alternatively, the complementary coupling features may comprise one of the recess and the collar comprising a male part and the other of the recess and the collar comprising a female part, at least one of the male part and the female part being arranged to resiliently deform as the collar is inserted into the recess such that the male part engages the female part to secure the collar to the recess. The collar and the recess may respectively comprise first and second anti-rotation features that interlock when the collar is inserted into the recess such that the collar cannot rotate within the recess.

The collar may be disc shaped and the attachment portions may be provided proximal to the periphery of the collar.

At least one of the plurality of attachment portions may comprise a suture hole arranged to receive and secure a first end of a suture.

At least one of the plurality of attachment portions may comprise an attached suture extending from the collar.

According to a second aspect of the present invention there is provided a prosthesis comprising: an implant according to any one of the preceding claims; and an arthroplasty implant having a distal portion arranged to be coupled to an end of a long bone and a proximal neck portion.

The neck portion may extend along an axis which is inclined to a longitudinal axis of the distal portion, and wherein when the collar is coupled to the articulation component and the articulation component is coupled to the proximal neck portion, the collar may lie in a plane which is perpendicular to the neck axis.

The arthroplasty implant may comprise an arthroplasty plate comprising a fixation plate arranged to be secured to a surface of a bone and a connector assembly extending from the fixation plate to form the proximal neck portion.

The connector assembly may comprise a barrel extending from the fixation plate with a bore which opens through the fixation plate and a connector rod arranged to slide within the bore of the barrel, and wherein the connector assembly may incorporate an adjustment mechanism arranged to cause the connector rod to slide into or out of the barrel and a locking mechanism arranged to lock the position of the connector rod within the barrel to rigidly space the articulation component apart from the fixation plate.

The fixation plate may comprise a head portion couplable to the connector assembly and an elongate body portion arranged to extend distally along the lateral surface of the bone, the elongate body portion comprising a plurality of fastener holes arranged to receive bone fasteners for securing the fixation plate to the bone.

The fixation plate head portion may comprise at least one suture hole arranged to receive a suture extending from the collar for securing bone fragments and soft tissues to the fixation plate and the collar.

The proximal neck portion may comprise a tapered portion and the reverse surface of the articulation component may comprise a corresponding tapered socket arranged such that when the end of the proximal neck portion is inserted into the tapered socket a taper lock forms securing the articulation component to the arthroplasty implant.

According to a third aspect of the present invention there is provided a surgical method comprising: removing at least part of an articulating surface at an end of a bone; coupling a distal portion of an arthroplasty implant to the end of the bone, the arthroplasty implant further comprising a proximal neck portion extending from the distal portion; securing bone fragments to a collar with sutures extending between the bone fragments or attached soft tissue and at least one of a plurality of attachment portions formed in the collar; coupling complementary features of the collar and a reverse surface of an articulation component together to secure the collar to the reverse surface, the articulation component further comprising a bearing surface; and coupling the articulation component to the proximal neck portion of the arthroplasty plate such that a neck hole of the collar passes around the coupling between the proximal neck portion of the arthroplasty implant and the articulation component.

Coupling a distal portion of an arthroplasty implant to the end of the bone may comprises: securing a fixation plate forming the distal part of the arthroplasty implant to a lateral surface of the fractured end of the bone, the fixation plate being coupled to a connector assembly defining the proximal neck portion and comprising a barrel with a bore and a connector rod, the connector rod being arranged to slide within the bore of the barrel; sliding the connector rod into or out of the barrel to adjust the length of the connector rod extending from the barrel; and locking the position of the connector rod within the barrel to rigidly space the articulation component apart from the fixation plate.

The fixation plate may further comprise a head portion proximal to the barrel, the head portion defining at least one suture hole, wherein the method may further comprise: threading sutures between the attachment portions of the collar and the at least one suture hole in the head portion of the fixation plate, the sutures passing through bone fragments or attached soft tissue to secure the bone fragments to the collar and the fixation plate.

The present invention will now be described, by way of example only, with reference to the accompanying drawings, in which:

FIGS. 6a to 6e illustrate steps of a surgical method for implanting the implant and arthroplasty plate of FIG. 2;

Figure 1:
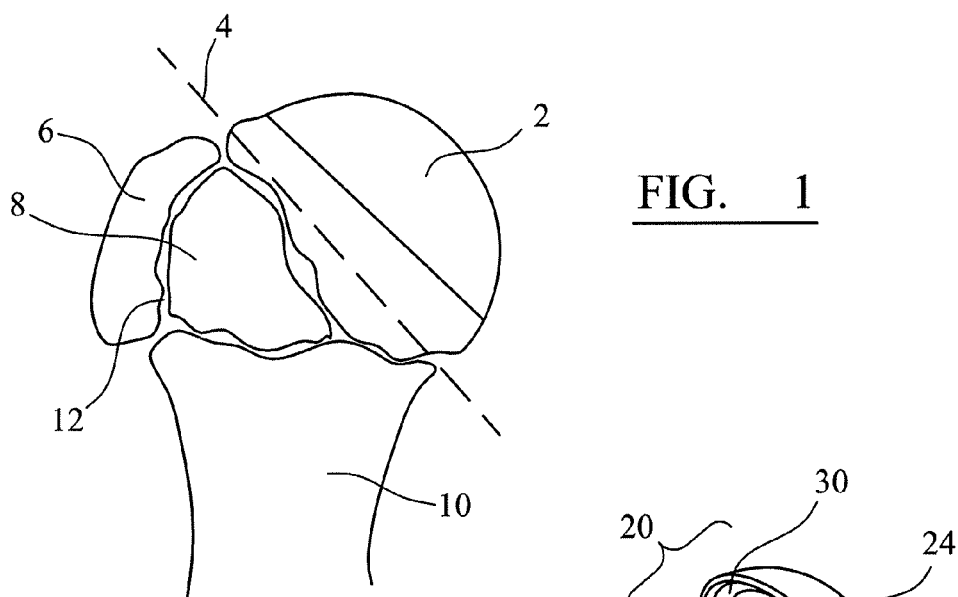
FIG. 1 illustrates a four part fracture of a proximal humerus.
Figure 2:
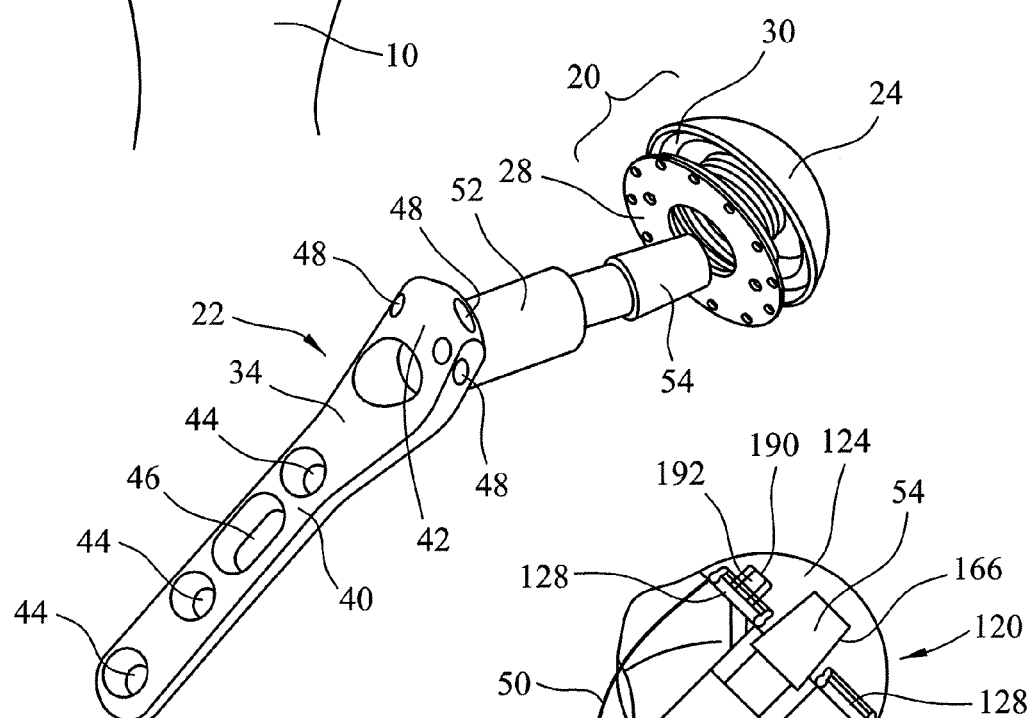
FIG. 2 illustrates an implant in accordance with a first embodiment of the present invention in combination with an arthroplasty plate.
Figure 3:
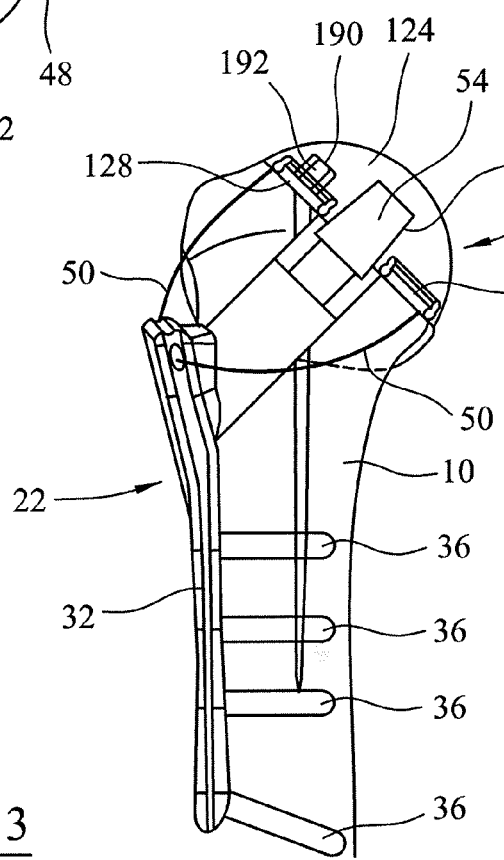
FIG. 3 shows an implant in accordance with a second embodiment of the invention and the arthroplasty plate of FIG. 2 implanted on an end of a humerus (the bone being illustrated as transparent to reveal the internal detail of the implanted arthroplasty plate)

Referring first to FIG. 2, this illustrates an implant 20 in accordance with a first embodiment of the present invention and an arthroplasty plate 22. The implant 20 comprises an articulation component 24 arranged to couple to a proximal neck portion 26 of the arthroplasty plate 22. The implant 20 further comprises a collar 28 arranged to be received in a recess 30 in a reverse surface of the articulation component 24. It will be appreciated that in alternative embodiments of the invention the collar may not be fully received in a recess or there may be no recess such that the collar simply couples to a reverse surface of the articulation component. FIG. 3 illustrates the arthroplasty plate 22 coupled to a lateral surface 32 of the proximal humerus 10 such that the proximal neck portion 26 extends through the fractured bone of a three or four part humeral fracture and couples to implant 20. FIG. 3 illustrates an implant 120 in accordance with a second embodiment of the present invention coupled to the arthroplasty plate 22. The first embodiment of the implant 20 is described below in greater detail in connection with FIGS. 4 and 5. The second embodiment of the implant 120 is described below in greater detail in connection with FIGS. 7 and 8.

The arthroplasty plate 22 is described in further detail in UK patent application 1101896.7 filed on 4 Feb. 2011 in the name of DePuy (Ireland), which is incorporated herein for all purposes. The arthroplasty plate 22 will also now be briefly described.

As noted above, conventional humeral implants for a shoulder prosthesis comprise a stem for insertion into a bore extending into the intramedullary canal of the humerus and an articulation component. The articulation component couples to a neck portion of the stem, which extends from the intramedullary canal at an inclined angle relative to the longitudinal axis of a distal portion of the stem. However, implanting a humeral stem into the intramedullary canal causes significant damage to the bone. An arthroplasty plate 22 as illustrated in FIGS. 2 and 3, and as described in greater detail in UK patent application 1101896.7 reduces the amount of natural bone that must be removed as the fixation plate 34 is secured to a lateral surface of the bone. The arthroplasty plate 22 incorporates a length adjustment feature which allows the distance between the humeral head implant 20 and the fixation plate 34 to be varied to adjust soft tissue tension in the shoulder joint and to optionally space the humeral head implant 20 away from the bone to avoid further damage to the fractured bone.

The humeral head implant 20 is coupled to the fixation plate 24 via a connector assembly 38 positioned in a bore formed in the proximal humerus 32. For repair of a three or four part humeral fracture the humeral shaft 10 is typically fractured below the greater and lesser tuberosities 6, 8. The fixation plate 34 is shaped such that the connector assembly 38 generally sits above the fracture line and so in practice it may not be necessary to form a bore, rather portions of the detached bone fragments may be trimmed to fit around the connector assembly 38.

The arthroplasty plate 22 is illustrated in a perspective view in FIG. 2. The fixation plate 34 comprises an elongate body portion 40 and a head portion 42 arranged to conform to the surface of the lateral humerus. The body portion 40 incorporates a number of screw holes 44 for securing the plate 40 to the humerus 32 with bone screws 36 as shown in FIG. 3. A slotted screw hole 46 is provided for initial fixation of the plate 40 to the bone. A screw is inserted into the bone through slotted hole 46 allowing the plate 40 to slide along the bone before the fixation plate 40 is permanently attached. Suture holes 48 are provided about the head portion 42 for securing soft tissues and bone fragments to the fixation plate 40. In particular, sutures 50 may extend from collar 28 to the head portion 42 of fixation plate 34 to retain bone fragments as illustrated in FIG. 3 and as will be described in greater detail below in connection with FIGS. 6a to 6e.

The plate 34 further comprises an integrally formed hollow barrel 52 extending from the plate transverse to the longitudinal axis of the plate, for instance at 135° to recreate the natural anatomy of the proximal humerus. The barrel 52 forms part of the connector assembly 38. The connector assembly 38 further comprises an adjustment mechanism to adjust the distance between a taper 54 and the fixation plate 34. The taper 54 is arranged to be received in a corresponding tapered socket in articulation component 24, as will be described in greater detail below. The connector assembly 38 further comprises a locking mechanism to lock the adjustment mechanism in position and prevent further movement between the taper 54 and the fixation plate 34. In combination the adjustment mechanism and the locking mechanism allow a surgeon to selectively space the articulation component 24 apart from the fixation plate 34 and then lock the components together such that the coupling is rigid. Advantageously the coupling allows the articulation component 24 to be spaced apart from the bone such that loads are transferred solely to the fixation plate, which may be desirable if the humeral head is badly fractured. The fixation plate 34 extends along the humerus sufficiently far to ensure that it can be secured to intact bone. Alternatively, the articulation component 24 may rest upon the bone such that load is partially transferred to the natural bone. The adjustment mechanism allows soft tissue tension within the reduced joint to be adjusted. The connector assembly 38 is not further described herein, but further details can be found within UK patent application 1101896.7.

Figure 4:
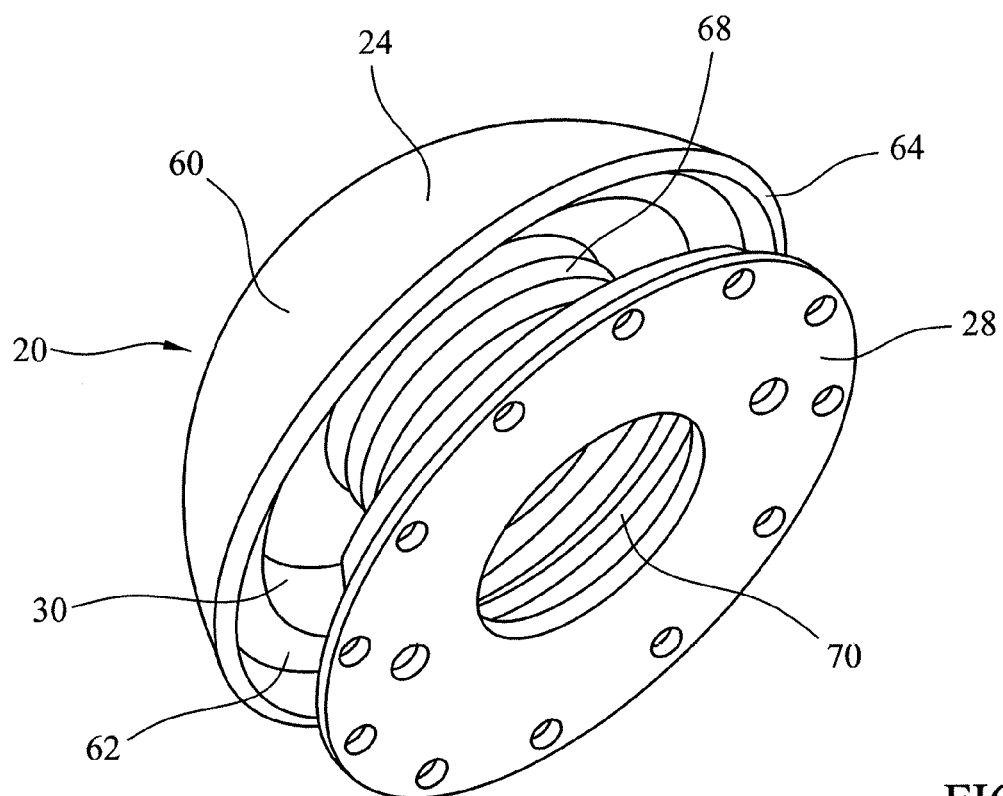
FIG. 4 is an exploded view of the implant of FIG. 2 showing a collar separated from an articulation component.
Figure 5:
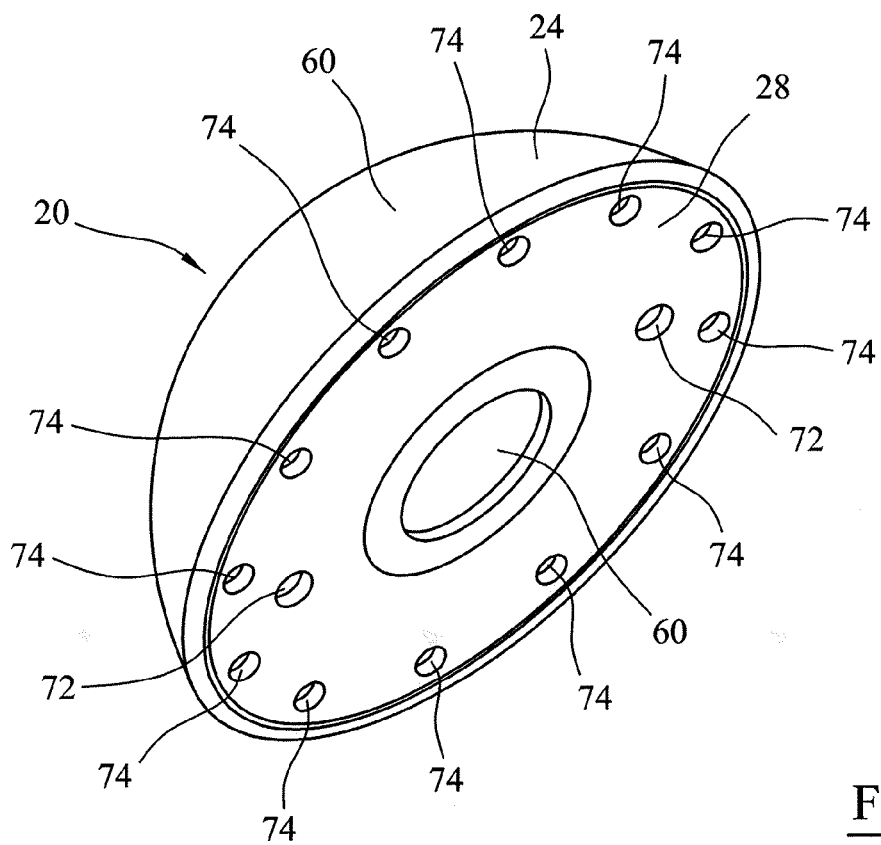
FIG. 5 is an assembled view of the implant of FIG. 2.

Referring now also to FIGS. 4 and 5, the first embodiment of a humeral head implant 20 will be described in greater detail. As noted above, the humeral head implant 20 comprises an articulation component 24 and a collar 28. FIG. 4 shows the articulation component 24 and collar 28 separated, and FIG. 5 shows the articulation component 24 and collar 28 coupled together.

The articulation component 24 comprises a convex bearing surface 60 and a reverse surface 62 that includes the recess 30. The convex bearing surface 60 may be defined by a portion of a sphere. The reverse surface 62 is substantially taken up by recess 30, which as illustrated extends across almost the full width of the reverse surface 62 within rim 64. The recess 30 extends about a socket 66 protrudes from the base of the recess to approximately the level of rim 64. Socket 66 defines a tapered bore and is arranged to form a taper lock to taper 54 at the end of the neck part 26 of arthroplasty plate 22. Specifically, during implantation, the articulation component 24 is placed so that taper 54 is received in socket 66 and an impaction force is applied to the convex bearing surface 60 to lock the two components together. It will be appreciated that in alternative embodiments of the invention the coupling between the socket 66 and the proximal neck portion 26 of the arthroplasty implant may vary, for instance they may be coupled by a screw thread or secured with a grub screw.

Recess 30 forms an annular ring about socket 66. The outer edge of socket 66 is provided with screw thread 68. Collar 28 comprises a threaded hole 70 such that rotating articulation component 24 while holding collar 28 still causes the collar to screw into recess 30 to lock the components together. When assembled, as shown in FIG. 5, the collar 28 is entirely received within recess 30 such that it is flush with rim 64, or recessed. Advantageously, this means that the convex bearing head can seat fully upon the bone, if required, unlike the collar disclosed in UK patent application 1007656.0. Collar 28 further comprises holes 72 to receive an instrument to hold the collar 28 still while coupling to the articulation component 24, as is described in greater detail below in connection with FIGS. 6d and 6e.

Around the periphery of collar 28 are suture holes 74. A suture can be threaded through one hole and back through a second hole to secure bone fragments and soft tissues such as cuff muscles to the collar, as will be described in greater detail below in connection with FIGS. 6a to 6e. The suture holes 74 may be evenly spaced apart about the whole periphery of collar 28 as illustrated, or they may be concentrated in portions of the collar which in use will be located near to particular bone fragments such as the greater and lesser tuberosities. The suture holes 74 may be approximately 2.5 mm in diameter. As illustrated in FIG. 3, the sutures may extend from suture holes 74 in the collar to suture holes 48 in the head part 42 of fixation plate 40. In an alternative embodiment, in place of or in addition to the suture holes 74, the collar 28 may have sutures 50 permanently coupled to or pre-attached to the collar 28. The sutures may be attached for instance by crimping or by being tied to a suture hole 74. Some or all of the pre-attached sutures may terminate at needles and/or anchors for coupling to bone or soft tissue, or alternatively conventional surgical techniques may be used to attach the sutures to bone or soft tissue. The needles or anchors may be entirely conventional and so will not be further described.

A surgical procedure for implanting the humeral head implant and arthroplasty plate of FIG. 2 to repair a fractured humeral head will now be described in connection with FIGS. 3 and 6a to 6e. It will be appreciated that details of the surgical procedure may vary, for instance according to the preferences of the surgeon. As discussed above, the arthroplasty plate and the humeral head implant of the present invention may be indicated for repair of three-part or four-part proximal humeral fractures. In a four-part proximal humeral fracture the humeral head is a free fragment not coupled to any soft tissue and deprived of a blood supply. The greater and lesser tuberosities are detached. The greater tuberosity is displaced superiorly and posteriorly by the attached rotator cuff, while the lesser tuberosity is retracted medially by the attached subscapularis. The fractured end of the humeral shaft is displaced medially by the pull of the pectoralis major. Three-part fractures differ in that the greater or lesser tuberosity remains attached to the humeral head, which in consequence is rotated internally by the subscapularis tendon.

The surgeon must first gain access to the fractured humeral head. The patient is positioned so as to allow the surgeon free access to the injured shoulder, for instance in a "beach chair" position, with the injured arm hanging free, providing spaced for later manipulation of the arm. The fracture may be examined using fluoroscopy, including under internal and external rotation. A deltopectoral exposure may be used to identify the coracoid, acromium and deltoid insertion. The interval between the pectoralis and the deltoid is developed and the incision line is extended distally from the coracoids.

The exposure is through a 12-14 cm incision. The incision may be held open using self retaining retractors. Care must be taken to identify and retract the cephalic vein. The coracobrachialis is retracted medially and the pectoralis insertion at the floor of the deltopectoral interval is located allowing the subacromial space to be developed to mobilise the proximal deltoid.

The detached humeral head may then be removed (after releasing the head from the greater or lesser tuberosity in the case of a three-part fracture). The humeral head implant 20 may be provided in a range of sizes to match the patient's natural humeral head. The appropriate size of articulation component 24 is selected, for instance by comparing the humeral head to a gauge to measure its height and radius of curvature. Each articulation component 24 may have a corresponding collar 28, or each articulation component may have a standard size recess 30 to receive a single size of collar 28. The tuberosities must also be released from underlying soft tissues, taking care to protect the axillary nerve when mobilising the lesser tuberosity and the attached subscapularis muscle tendon. The tuberosities are released so as to allow them to be coupled to each other and to the arthroplasty plate, passing around the prosthesis.

A surgical technique for implanting the arthroplasty plate is described in greater detail in UK patent application 1101896.7 but is also summarised here. Initially a trial plate is applied to the surface of the humerus. The trial plate may be generally the same as the fixation plate 34, and in particular the bone contacting surface may be the same shape. However, the trial plate does not include a barrel 52 and so it may be freely positioned over the surface of the proximal, lateral humerus. The anterior side of the trial plate is aligned with the bicipetal groove.

The trial plate further comprises a guide arranged to guide a 2 mm guide wire. The guide wire indicates where the prosthetic head (articulation component 24) will be centred. This allows the surgeon to see that the trial head will be in the correct position in relation to the calcar region and the tuberosities. The guide wire is advanced slowly and the trajectory may be verified under fluoroscopy. The guide wire serves to temporarily secure the trial plate to the bone. A trial head may be coupled to the guide wire. When correctly positioned the inferior aspect of the trial head should align with the medial end of the humeral head.

Once the position of the trial head has been confirmed, the surgeon may be required to remove remaining fragments of the articulation surface of the humeral head. Typically, the articulation surface may already be fractured or detached from the humerus. If required, a drill reamer may be used to form a bore to receive the barrel 52. Alternatively, the barrel 52 may extend above the fracture line of the humeral shaft 10, or minimal bone removal may be required.

The fixation plate 34 may then be secured to the lateral humeral surface with the connector assembly 38 extending towards the original position of the humeral head. The trial head 208 may be temporarily coupled to the taper 54 to check the final position of the neck axis.

The position of the trial head may then be adjusted using the adjustment mechanism within the connector assembly 38 to determine the required position for the humeral head implant 20. The position of the trial head may either be determined before or after the shoulder joint is reduced, or further adjustment may be performed after the shoulder joint is reduced. The connector assembly is then locked in position and the trial head removed.

Figure 6D:
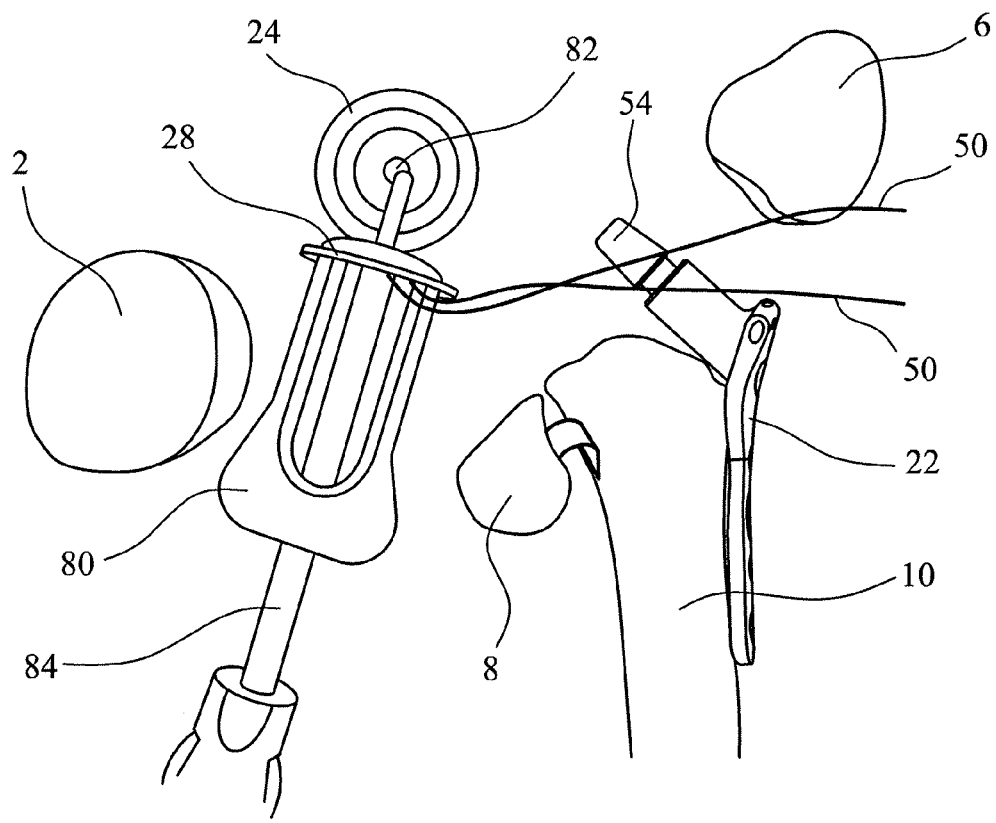

Referring to FIG. 6a, after the arthroplasty plate has been secured to the bone, the collar 28 is coupled to the bone fragments, and in particular the greater and lesser tuberosities with sutures 50. FIG. 6a shows the collar 28 threaded with five sutures 50, and the tuberosities are not shown. Initially the sutures are loosely coupled to the bone fragments to allow the collar 28 to be manoeuvred to be secured to the articulation component 24, as shown in FIG. 6b. As the sutures may pull through tuberosity fragments in osteoporotic bone, preferably the sutures are additionally or only passed through the cuff tendons. For the humeral head implant 20 of the first embodiment of the invention, the articulation component 24 is screwed onto the collar 28 while the collar 28 is held still, as will be described below in connection with FIGS. 6d and 6e. The humeral head implant 20 is then secured to the arthroplasty plate 22 as shown in FIG. 6c (illustrated without the bone for clarity) by inserting taper 54 into the socket 60 and applying an impaction force to the humeral head implant 20. The sutures 50 coupling the bone fragments to the collar 28 are then secured to the arthroplasty plate 22 and tightened to form a cage of sutures surrounding the bone fragments. The suture cage provides additional rigidity to the coupling between the arthroplasty plate 22 and the humeral head implant 20.

Figure 6E:
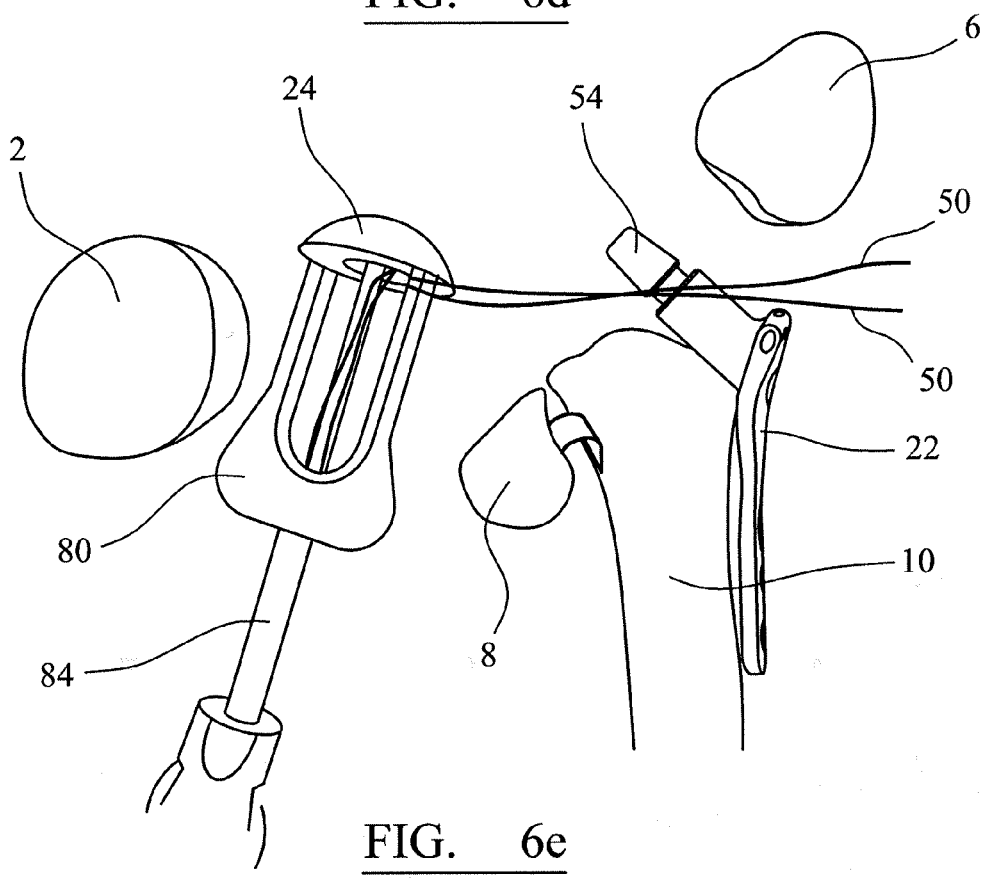

Referring to FIG. 6d, the arthroplasty plate 22 is shown secured to the humerus shaft 10 and the sutures 50 are coupled to the collar 28. For clarity the greater and lesser tuberosities 6, 8 are not coupled to the sutures 50. The fractured humeral head 2 is shown removed from the humerus. The collar 28 is held still using a collar handle 80 which has twin prongs (not visible) arranged to engage holes 72. The articulation component 24 has a hexagonal slot 82 at the base of socket 60 arranged to be engaged by a driver 84 to rotate the articulation component 24 relative to the collar 28 to secure screw threads 68, 70 as shown in FIG. 6e. It will be understood that the sutures 50 must be kept loose until after the articulation component 24 has been screwed onto collar 28 to allow space for the driver 84 to access the slot 82.

Compression, if required, between the articulation component 24 and the tuberosities may be provided by adjusting the distance between taper 54 and the fixation plate 34 using the adjustment mechanism within the connector assembly 38. Alternatively, the articulation component 24 may be moved away from the fixation plate 34 to tension the sutures 50 extending between the collar 28 and the head portion 42 of the arthroplasty plate 22.

Figure 7:
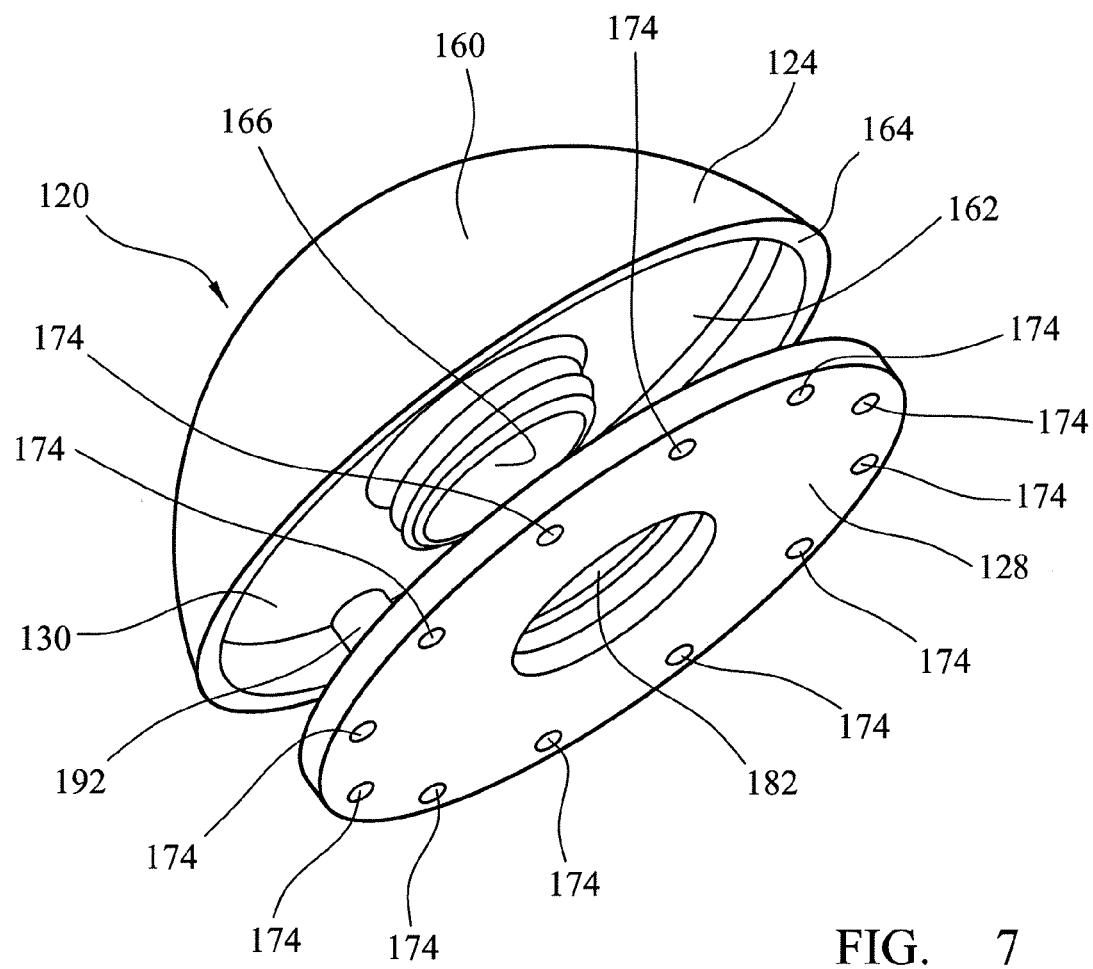
FIG. 7 is an exploded view of an implant in accordance with the second embodiment of the present invention illustrated in FIG. 3.
Figure 8:
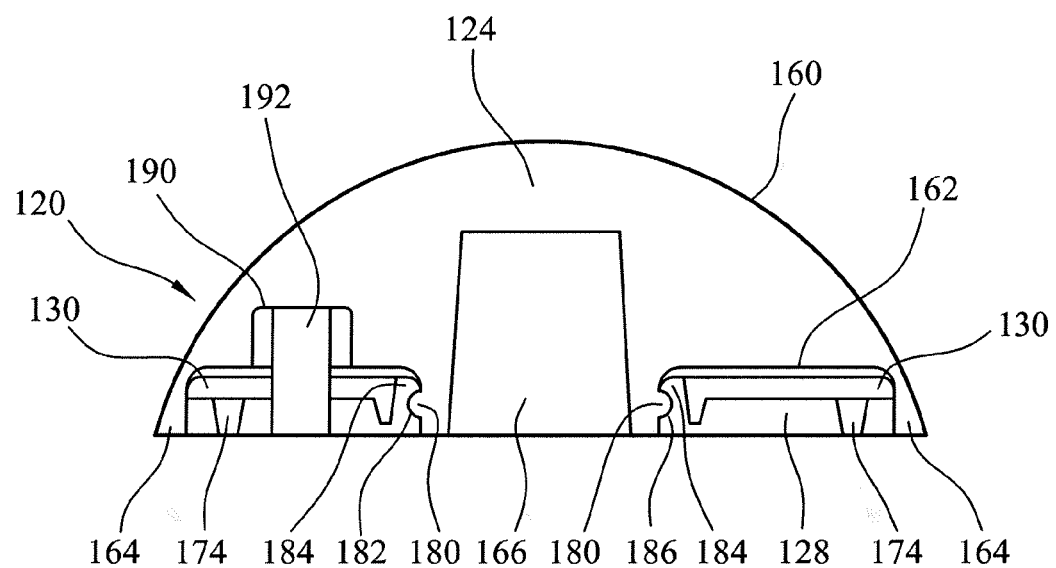
FIG. 8 is a cross sectional view of the assembled implant of FIG. 7.

Referring now to FIGS. 7 and 8, these illustrate a humeral head implant 120 in accordance with a second embodiment of the present invention. The second humeral head implant 120 is generally similar to the implant 20 illustrated in FIGS. 4 and 5, and so corresponding features are identified by the same reference numbers incremented by 100. As for the first embodiment, humeral head implant 120 comprises an articulation component 124 and a collar 128. FIG. 7 shows the articulation component 124 and collar 128 separated, and FIG. 8 shows a cross section when coupled together. FIG. 3 additionally illustrates the second embodiment 120 of the present invention when coupled to an arthroplasty plate 22.

The articulation component 124 comprises a convex bearing surface 160 and a reverse surface 162 that includes recess 130. The convex bearing surface 160 may be defined by a portion of a sphere. The reverse surface 162 is substantially taken up by recess 130, which as illustrated extends across almost the full width of the reverse surface 162 within rim 164. The recess 130 extends about socket 166 which is tapered and arranged to form a taper lock to taper 54 at the end of the neck part 26 of arthroplasty plate 22.

Recess 130 forms an annular ring about socket 166. The outer edge of socket 166 is provided with an annular rib 180. Collar 128 comprises a hole 182 defined by a raised rim 184 corresponding to the outer shape of socket 166 and including an annular groove 186. Rim 184 is resiliently deformable such that when forced over socket 166 it expands to allow groove 186 to engage rib 180. Collar 128 snap fits to articulation component 124 such that after the collar has been sutured to bone fragments and soft tissue the collar can be coupled to the articulation component 124 before the articulation component 124 is coupled to taper 54. When assembled, as shown in FIG. 8, the collar 128 is entirely received within recess 130 such that it is flush with rim 164, or recessed.

The articulation component 124 further comprises a hole 190 within the recess 130 and the collar 128 comprises a pin 192 arranged to be received within the hole 190. The pin and hole prevent the collar from rotating relative to the articulation component when they are coupled together.

Around the periphery of collar 128 are suture holes 174. As for the first embodiment of the humeral head implant, sutures may be pre-attached to the collar. If sutures are supplied pre-attached to the collar then the articulation component may be coupled to the collar before the implant is passed to the surgeon. However, an advantage of providing a separate collar is that the size of the implant is reduced when securing bone fragments and soft tissues in position, which provides the surgeon with more space to operate.

In addition to the screw fit and snap fit options for securing the collar to the articulation component described above, it will be readily apparent that the two components can be coupled together in other ways. For instance, the recess in the reverse surface of the articulation component may taper and the collar may have a tapered edge and/or tapered neck hole to form a taper lock with the recess. Alternatively they may be secured with screws or bolts, for instance passing through the collar into the reverse surface of the articulation component. Other coupling options will be readily apparent to the appropriately skilled person.

The implant of the present invention has been primarily described above as forming part of a humeral prosthesis. The implant is particularly suitable for the repair of shoulder fracture indications because there are typically three or four portions of fractured bone, and so the collar assists in retaining the bone fragments. However, the implant may also form part of a modular prosthesis for implantation at the end of another long bone. For instance, the collar may form part of a femoral prosthesis for the repair of hip fractures. Commonly, the femur fractures across the neck. However, for some forms of femoral fracture, there are multiple portions of fractured bone and so the implant of the present invention may be useful for fixing the bone fragments in position.

Other modifications to, and applications of, the present invention will be readily apparent from the teaching herein without departing from the scope of the appended claims.

The invention claimed is:

1. A surgical method comprising the steps of:
    removing at least part of an articulating surface at an end of a bone;
    coupling a distal portion of an arthroplasty implant to the end of the bone, the arthroplasty implant comprising a proximal neck portion extending from the distal portion;
    securing bone fragments to a collar with sutures extending between the bone fragments or attached soft tissue and at least one of a plurality of attachment portions formed in the collar;
    coupling complementary features of the collar and a reverse surface of an articulation component together to secure the collar to the reverse surface, the articulation component further comprising a bearing surface; and coupling the articulation component to the proximal neck portion of the arthroplasty implant such that a neck hole of the collar passes around the coupling between the proximal neck portion of the arthroplasty implant and the articulation component; and wherein the step of securing the bone fragments to the collar is performed with the articulation component detached from the collar.

2. The surgical method of claim 1, wherein the step of coupling the distal portion of an arthroplasty implant to the end of the bone comprises securing a fixation plate forming the distal part of the arthroplasty implant to a lateral surface of the fractured end of the bone, the fixation plate being coupled to a connector assembly defining the proximal neck portion and comprising a barrel with a bore and a connector rod, the connector rod being arranged to slide within the bore of the barrel;

sliding the connector rod into or out of the barrel to adjust the length of the connector rod extending from the barrel; and locking the position of the connector rod within the barrel to rigidly space the articulation component apart from the fixation plate.

3. The surgical method of claim 2, wherein the fixation plate further comprises a head portion proximal to the barrel, the head portion defining at least one suture hole, wherein the method further comprises the step of threading sutures between the attachment portions of the collar and the at least one suture hole in the head portion of the fixation plate, the sutures passing through bone fragments or attached soft tissue to secure the bone fragments to the collar and the fixation plate.

4. The surgical method of claim 1 wherein the arthroscopy implant comprises a fixation plate and the step of coupling the distal portion of the arthroscopy implant to the distal end of the bone comprises securing the fixation plate to an outer surface of the bone.

5. The surgical method of claim 1 wherein the sutures between the bone fragments and the collar form a cage of suture surrounding the bone fragments.

6. The surgical method of claim 1 and further comprising the step of attaching the sutures between the collar and the arthroscopy implant.

* * * * *